United States Patent
Bharat et al.

(10) Patent No.: US 11,096,745 B2
(45) Date of Patent: Aug. 24, 2021

(54) SYSTEM AND WORKFLOW FOR GRID-LESS TRANSPERINEAL PROSTATE INTERVENTIONS

(71) Applicant: KONINKLIJKE PHILIPS N.V., Eindhoven (NL)

(72) Inventors: Shyam Bharat, Arlington, MA (US); Aleksandra Popovic, Cambridge, MA (US); Ameet Kumar Jain, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 344 days.

(21) Appl. No.: 15/776,921

(22) PCT Filed: Nov. 29, 2016

(86) PCT No.: PCT/IB2016/057174
§ 371 (c)(1),
(2) Date: May 17, 2018

(87) PCT Pub. No.: WO2017/093885
PCT Pub. Date: Jun. 8, 2017

(65) Prior Publication Data
US 2018/0325602 A1 Nov. 15, 2018

Related U.S. Application Data

(60) Provisional application No. 62/263,160, filed on Dec. 4, 2015.

(51) Int. Cl.
*A61B 34/20* (2016.01)
*A61B 34/00* (2016.01)
*A61B 34/10* (2016.01)
*A61B 17/34* (2006.01)
(Continued)

(52) U.S. Cl.
CPC ............. *A61B 34/20* (2016.02); *A61B 34/10* (2016.02); *A61B 34/70* (2016.02); *A61B 8/12* (2013.01);
(Continued)

(58) Field of Classification Search
CPC ......... A61B 34/20; A61B 34/10; A61B 34/70; A61B 8/12; A61B 8/4218; A61B 8/4209;
(Continued)

(56) References Cited

U.S. PATENT DOCUMENTS 5,647,373 A * 7/1997 Paltieli ................... A61B 8/00
600/461
7,306,557 B2 12/2007 Lagendijk et al.
(Continued)

*Primary Examiner* — Amelie R Davis
(74) *Attorney, Agent, or Firm* — Sherry Austin

(57) ABSTRACT

A transperinealprostate intervention device comprises a prostate intervention instrument (10), a transrectal ultrasound (TRUS) probe (12), and a mechanical or optical coordinate measurement machine (CMM) (20) attached to the TRUS probe and configured to track the prostate intervention instrument. The CMM may include an articulated arm with a plurality of encoding joints (24), an anchor end (30) attached to the TRUS probe, and a movable end (32) attached to the prostate intervention instrument. The prostate intervention instrument may, for example, be a biopsy needle, a brachytherapy seed delivery instrument, a tissue ablation instrument, or a hollow cannula. An electronic processor (40) computes a predicted trajectory (54) of the prostate intervention instrument in a frame of reference of the TRUS probe using the CMM attached to the TRUS probe. A representation (56) of the predicted trajectory is superimposed on a prostate ultrasound image (50) generated from ultrasound data collected by the TRUS probe.

15 Claims, 3 Drawing Sheets

(51) Int. Cl.
    *A61B 34/30*     (2016.01)
    *A61B 90/00*     (2016.01)
    *A61B 8/12*     (2006.01)
    *A61B 8/00*     (2006.01)

(52) U.S. Cl.
    CPC .......... *A61B 8/4209* (2013.01); *A61B 8/4218* (2013.01); *A61B 2017/3413* (2013.01); *A61B 2034/107* (2016.02); *A61B 2034/2059* (2016.02); *A61B 2034/302* (2016.02); *A61B 2090/3782* (2016.02)

(58) Field of Classification Search
    CPC ...... A61B 2017/3413; A61B 2034/302; A61B 2034/107; A61B 2034/2059; A61B 2090/3782
    See application file for complete search history.

(56) References Cited

U.S. PATENT DOCUMENTS

| | | |
|---|---|---|
| 8,521,257 B2 | 8/2013 | Whitcomb et al. |
| 9,623,261 B2 | 4/2017 | Van De Wardt et al. |
| 9,943,708 B2 | 4/2018 | Roberts et al. |
| 2009/0069945 A1 | 3/2009 | Burgkart |
| 2009/0198094 A1* | 8/2009 | Fenster .................... A61B 8/12 600/3 |
| 2009/0234369 A1* | 9/2009 | Bax ........................ A61B 90/11 606/130 |
| 2010/0298705 A1* | 11/2010 | Pelissier .................. A61B 8/42 600/443 |
| 2013/0190623 A1 | 7/2013 | Bertolina et al. |
| 2014/0121675 A1 | 5/2014 | Bax et al. |
| 2015/0065886 A1 | 3/2015 | Stoianovici |

\* cited by examiner

//www.w3.org/1999/xhtml">
SYSTEM AND WORKFLOW FOR GRID-LESS TRANSPERINEAL PROSTATE INTERVENTIONS

CROSS-REFERENCE TO PRIOR APPLICATIONS

This application is the U.S. National Phase application under 35 U.S.C. § 371 of International Application Serial No. PCT/IB2016/057174, filed on Nov. 29, 2016, which claims the benefit of U.S. Patent Application No. 62/263,160, filed on Dec. 4, 2015. This application is hereby incorporated by reference herein.

FIELD

The following relates generally to the medical arts, oncology arts, prostate cancer intervention arts, and related arts.

BACKGROUND

Focal prostate intervention targets suspected or known prostate cancer tumors or regions, rather than targeting the prostate organ as a whole. A conventional approach for focal prostate intervention is to employ a transrectal ultrasound (TRUS) probe inserted into the rectum for imaging the prostate. A grid with needle openings is placed against the perineum (the external body surface generally delineated between the legs, anus and scrotum) with the grid spatially registered with the TRUS image. An interventional instrument (e.g. a biopsy needle, brachytherapy seed delivery needle, RF ablation or cryoablation instrument, hollow cannula providing a conduit for such, or so forth) is aligned by the grid and inserted through the perineum into the prostate.

This grid-based approach is generally effective, but has some drawbacks. The angle of insertion of the interventional instrument is fixed by the grid, and thus multiple insertions at non-parallel or arbitrary angles is not usually possible. In particular, the presence of the pubic arch or other anatomical constraints may necessitate novel angular approaches for a particular patient.

The following discloses a new and improved systems and methods that address the above referenced issues, and others.

SUMMARY

In one disclosed aspect, a transperineal prostate intervention guidance device comprises a transrectal ultrasound (TRUS) probe including an ultrasound transducer or transducer array, a coordinate measurement machine (CMM) configured for attachment to the TRUS probe and configured to track the position and orientation of a prostate intervention instrument in a frame of reference of the TRUS probe, and an electronic processor programmed to compute a predicted trajectory of the prostate intervention instrument in the frame of reference of the TRUS probe using the CMM, and generate a prostate ultrasound image from ultrasound data collected by the TRUS probe with a representation of the predicted trajectory of the prostate intervention instrument superimposed on the prostate ultrasound image.

In another disclosed aspect, in a transperineal prostate intervention guidance device as set forth in the immediately preceding paragraph the CMM comprises an articulated arm including arm segments connected by encoding joints and having an anchor end configured for attachment to the TRUS probe and a movable end configured for attachment with the prostate intervention instrument. The electronic processor is programmed to compute the predicted trajectory from a position and orientation of the movable end of the articulated arm determined from encoding values of the encoding joints.

In another disclosed aspect, a transperineal prostate intervention device comprises a prostate intervention instrument, a transrectal ultrasound (TRUS) probe including an ultrasound transducer or transducer array, and a mechanical or optical coordinate measurement machine (CMM) attached to the TRUS probe and configured to track the prostate intervention instrument. A mechanical CMM embodiment includes an articulated arm with a plurality of encoding joints (at least three encoding joints in some such embodiments), an anchor end attached to the TRUS probe, and a movable end attached to the prostate intervention instrument. The prostate intervention instrument may, for example, be a biopsy needle, a brachytherapy seed delivery instrument, or a tissue ablation instrument. An electronic processor may be programmed to compute a predicted trajectory of the prostate intervention instrument in a frame of reference of the TRUS probe using the mechanical or optical CMM attached to the TRUS probe. A representation of the predicted trajectory may be superimposed on a prostate ultrasound image generated from ultrasound data collected by the TRUS probe.

In another disclosed aspect, a transperineal prostate intervention guidance method is disclosed. An ultrasound image of a prostate is displayed that is generated from ultrasound data acquired by a transrectal ultrasound (TRUS) probe. During the displaying, a predicted trajectory of a prostate intervention instrument is computed in a frame of reference of the TRUS probe using a mechanical or optical coordinate measurement machine (CMM) anchored to the TRUS probe. A representation of the predicted trajectory of the prostate intervention instrument is superimposed on the displayed ultrasound image of the prostate. The computing and superimposing operations may be performed with no portion of the prostate intervention instrument in the field of view of the ultrasound image.

One advantage resides in providing focused prostate intervention using an interventional instrument having a flexible positional and angular approach.

Another advantage resides in providing improved interventional instrument trajectory prediction for focused prostate intervention.

Another advantage resides in providing multiple redundant tracking of the interventional instrument during focused prostate intervention.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 1 shows the device prior to penetration of the perineum by the interventional instrument. FIG. 2 shows the device after penetration of the perineum by the interventional instrument.

DETAILED DESCRIPTION

Figure 1:
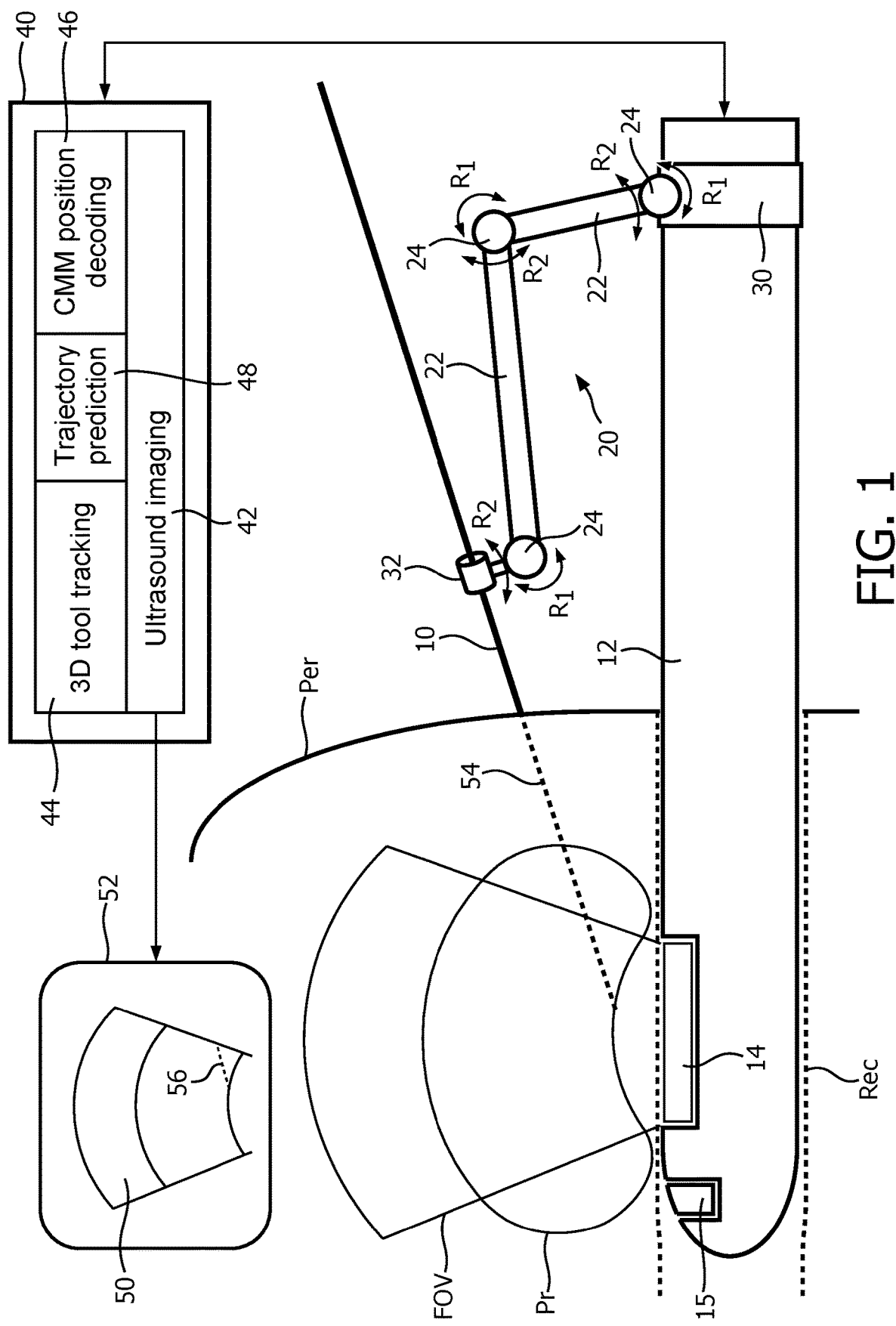
FIGS. 1 and 2 diagrammatically show an illustrative transperineal prostate intervention device.
Figure 2:
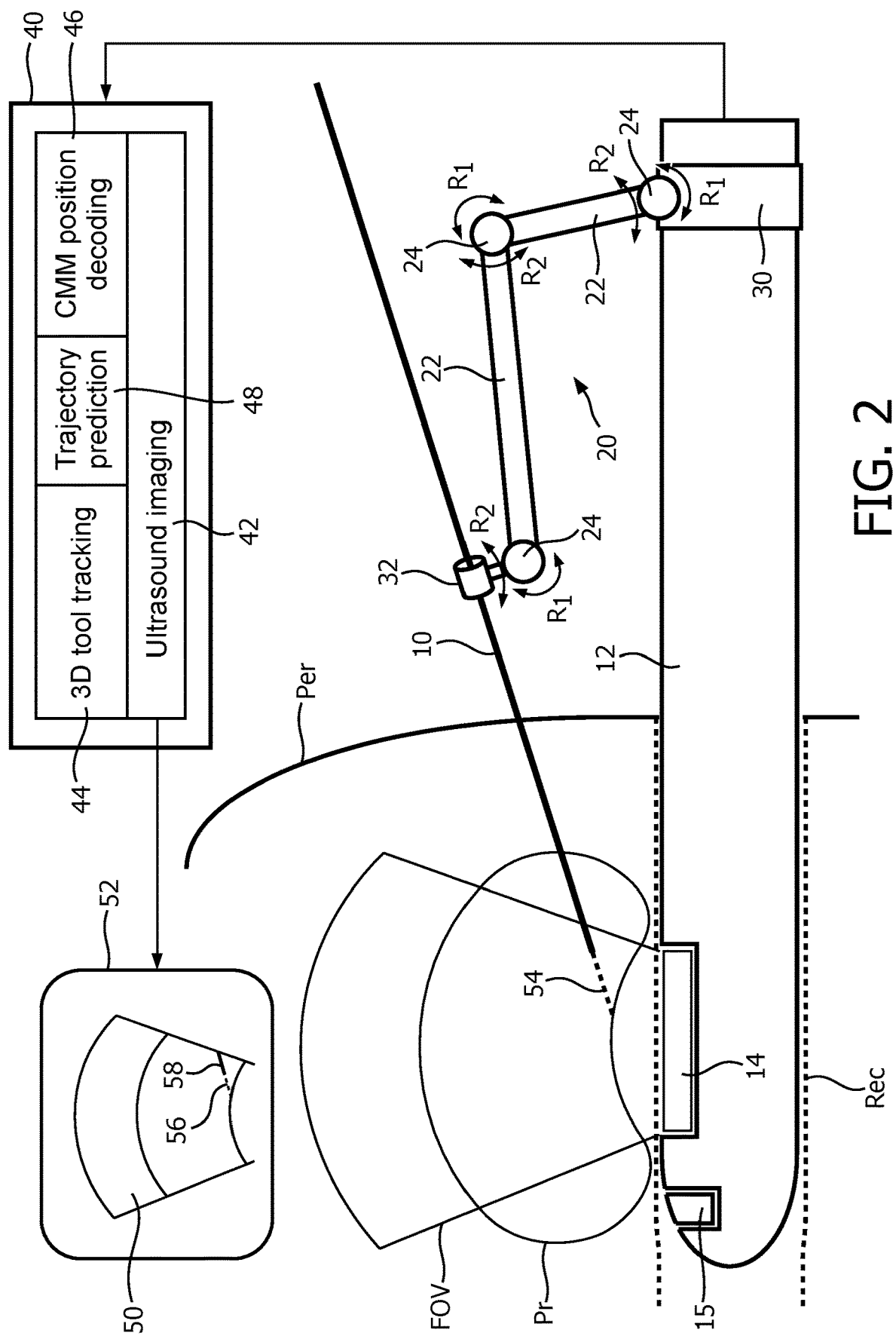

With reference to FIGS. 1 and 2, an illustrative transperineal prostate intervention device includes a transperineal prostate intervention device. The device includes a prostate intervention instrument 10, and a transperineal prostate intervention guidance device that includes a transrectal ultrasound (TRUS) probe 12 with an ultrasound transducer or transducer array 14, 15. The illustrative TRUS probe 12 includes a sagittal ultrasound transducer array 14 and an axial ultrasound transducer array 15. During a transperineal prostate intervention procedure, the TRUS probe 12 is partially inserted into the rectum Rec of a patient undergoing the prostate intervention, with the inserted end of the TRUS probe 12 carrying the ultrasound transducer(s) 14, 15 inside the rectum Rec of the patient and into position to acquire ultrasound data to generate an ultrasound image with a field of view (FOV) that intersects or contains at least a portion of the prostate Pr of the patient. The illustrative example employs the sagittal ultrasound transducer array 14 to acquire a planar brightness-mode (B-mode) image in the FOV, but this is merely an illustrative example and other ultrasound imaging modes, optionally with chosen post-acquisition processing, may be used to perform ultrasound imaging of the prostate Pr using ultrasound data collected using the TRUS probe 12. The transperineal prostate intervention procedure entails penetration of the perineum Per by (an end of) the interventional instrument 10. FIG. 1 shows the device prior to penetration of the perineum Per by the interventional instrument 10. FIG. 2 shows the device after penetration of the perineum Per by the interventional instrument 10. By way of some non-limiting illustrative examples, the transperineal prostate intervention procedure may be a prostate biopsy procedure in which case the interventional instrument 10 is a biopsy needle; or may be a brachytherapy procedure in which case the interventional instrument 10 is a brachytherapy seed delivery instrument; or may be a tissue ablation procedure (e.g. cryoablation, radio frequency ablation, or so forth) in which case the interventional instrument 10 is a tissue ablation instrument; or so forth. The interventional instrument 10 may also be a hollow cannula that accommodates one or more of the interventional biopsy/therapy instruments mentioned above (i.e., biopsy needle, brachytherapy needle, ablation needle etc.).

The transperineal prostate intervention guidance device further includes a coordinate measuring machine (CMM) 20 for measuring the position and orientation of the interventional instrument 20 in a frame of reference of the TRUS probe 12. The illustrative CMM 20 is a portable CMM comprising an articulated arm made up of a plurality of arm segments 22 (e.g. rods, beams, tubes, or so forth) connected by encoding joints 24, e.g. rotary joints with sensors outputting the current joint angle or angles. The CMM 20 has an anchor end 30 connected to an arm segment or (as illustrated) to a joint 24 which is configured by a clamp or other mount to be secured to (i.e. "anchored" to) the portion of the TRUS probe 12 extending outside of the rectum Rec. The CMM 20 further has an opposite movable end 32 connected to an arm segment or (as illustrated) to a joint 24 and configured by a collar or other mount for attachment with the prostate intervention instrument 10. The articulated arm is designed to provide three-dimensional freedom of movement of the movable end 32 while the anchor end 30 remains anchored to its tether point (the TRUS probe 12 in the illustrative example). By way of illustration, each illustrated joint 24 has two encoded angular adjustment directions: a first encoded angular adjustment direction $R_{sub.1}$ by which the angle between the two connected arm segments 22 (or between the connected arm segment 22 and the connected end 30 or end 32) is adjusted, and a second angular adjustment direction $R_{sub.2}$ in which one arm segment 22 or end 32 can be rotated about its axis. These are merely illustrative articulations, and the articulated arm of the CMM may have other articulation architectures with different numbers of joints, and different numbers or type(s) of movement(s) for each joint or for different joint. For example, in addition to the angular adjustments $R_{sub.1}$ and $R_{sub.2}$, a third angular adjustment $R_{sub.3}$ could be provided by which links may be moved in a direction perpendicular to the plane of the robotic arm in its shape shown in FIG. 1. (That is, $R_{sub.3}$ would provide movement "in or out of the page" of FIG. 1. This third angular adjustment direction would roughly correspond to motion in the lateral or "L-R" direction with respect to the perineum/prostate.) Each encoded movement provides a degree of freedom for the articulated arm, and the CMM 20 preferably has at least two joints, and in the illustrative example has three joints 24, providing a number of degrees of freedom (six degrees of freedom in the illustrated CMM 20—$R_{sub.1}$ and $R_{sub.2}$ for each of the three joints 24) sufficient to provide flexible three-dimensional movement of the interventional instrument 10. By way of non-limiting example, some portable CMM that are suitable for use as the CMM 20 include the MicroScribe® CMM line of portable CMM systems available from Revware Systems, Raleigh, N.C., USA.

The transperineal prostate intervention guidance device further includes an electronic processor 40, which may for example be an ultrasound imaging device including a microprocessor or microcontroller. The electronic processor 40 is programmed to perform various guidance functions, including: ultrasound imaging 42; optional three-dimensional (3D) tracking 44; CMM position (and orientation) decoding 46; and trajectory prediction 48. These functions and their interactions are described below.

The ultrasound imaging 42 operates the TRUS probe 12 to generate a prostate ultrasound image 50 (optionally comprising video) of at least a portion of the prostate Pr. The prostate ultrasound image 50 is displayed on a display component 52, e.g. an LCD display or other display component of the ultrasound imaging device.

The optional 3D tracking 44 tracks the location of the interventional instrument 10 when it is in the FOV of the image 50. This component is optional because, depending upon the type and material of the interventional instrument 10 and the type of ultrasound imaging 42 being performed, in some embodiments the portion of the interventional instrument 10 in the FOV of the image 50 is visible in the ultrasound image in such cases there is no need for 3D tracking 44 to be performed since the surgeon can directly observe the portion of the interventional instrument extending into the FOV of the prostate ultrasound image 50. Even if the interventional instrument is not observable in the image, its position can be determined by the CMM position decoding 46 as will be described, so that the 3D tracking 44 may again optional. On the other hand, tracking of the inserted interventional instrument using the CMM can be problematic as it operates on the assumption that the interventional instrument remains straight as it passes through the perineum and into the prostate. The CMM-based tracking will not detect any bending of the instrument, whereas the 3D tracking can detect such bending in the FOV of the image 50. If provided, the 3D tracking 44 determines position and orientation of a portion of the prostrate intervention instrument 10 in the FOV of the prostate ultrasound image 50 using ultrasound signals generated in response to ultrasound transmissions output by the TRUS probe 12. In one approach, these ultrasound signals are the prostate ultrasound image, which may be segmented to determine the position of the interventional instrument. In other embodiments these signals may be generated by ultrasound sensors (not shown) disposed on the prostate intervention instrument 10 in response to ultrasound transmissions output by the TRUS probe. Such 3D tool tracking is described, for example, in Mung et al., "A Non-Disruptive Technology for Robust 3D Tool Tracking for Ultrasound-Guided Interventions", MICCAI 2011, Part I, LNCS 6891, pp. 153-160 (2011).

The CMM position decoding 46 determines the position and orientation of the interventional instrument 10 from the position and orientation of the movable end 32 of the CMM 20 determined from the encoded angular positions $R.sub.1$, $R.sub.2$ of the joints 22. If the CMM 20 is a commercial product such as the MicroScribe® CMM, the position and orientation of the movable end 32 may be reported by commercial control software for the CMM 20; more generally, the position and orientation can be computed by starting at the known fixed position of the anchor end 30 and determining the position and orientation of the next arm segment 22 based on the angular positions (or more generally, encoding values) of the connecting joint 24, and continuing in this fashion from one arm segment to the next until the last operation determines the position and orientation of the movable end 32 based on the encoding values of the last connecting joint 24. This processing provides the position and orientation of the movable end 32 of the CMM 20; the position and orientation of the interventional instrument 10 can then be inferred since it is secured to the movable end 32 and hence has a fixed position and orientation respective to the movable end 32. As all processing is referenced to the anchor end 30 of the CMM 20 which is secured to the TRUS probe 12, the resulting CMM-determined position and orientation of the interventional instrument 10 is in the frame of reference of the TRUS probe 12.

The illustrative CMM 20 employing an articulated arm comprising arm segments 22 and encoding joints 24 is an illustrative example. Other types of CMM which can be secured to the TRUS probe 12 could alternatively be used. As another illustrative example, the CMM could be an optical CMM comprising a camera or other set of optical sensors arranged to optically view the tip of the interventional instrument 10 from a range of different angles (typically at least three different angles are needed). In this case, the CMM position decoding 46 suitably employs three-dimensional triangulation to determine the position and orientation of the interventional instrument 10 from the different vantage points. An advantage of an optical CMM is that no arm is physically connected with the interventional instrument 10; a disadvantage is that if the surgeon's hands manipulating the instrument 10 block the view of one or more optical sensors of the optical CMM then this may interrupt operation of the CMM position decoding 46.

As a different contemplated variant, the CMM 20 including an articulated arm as illustrated could be used, but with the joints 24 being motor-operated so that the articulated arm is a robotic arm. In this case the surgeon could use the robotic arm to manipulate the interventional instrument 10, for example controlling it using a joystick.

After the position and orientation of the interventional instrument 10 is determined by the CMM position decoding 46, the trajectory prediction 48 then operates to predict a trajectory 54 (see FIG. 1) of the interventional instrument 10 in the prostate Pr. Typically, the end of the interventional instrument 10 designed to penetrate through the perineum Per and into the prostate Pr is straight, e.g. a straight biopsy needle, or a straight hollow tube defining the operational end of a brachytherapy seed delivery instrument, or a tissue biopsy instrument with a straight needle terminating in an RF ablation emitter or a cryo-tip, or so forth. The straight end facilitates insertion into tissue with minimal damage. Accordingly, the trajectory prediction 48 operates by computing a linear extension of the known position and orientation of the straight end of the interventional instrument 10 until it intersects into the known spatial volume containing the prostate Pr. This latter is determined from the prostate ultrasound image 50, taking advantage of the CMM-determined position and orientation of the interventional instrument 10 being in the frame of reference of the TRUS probe 12 which is also the frame of reference for the prostate ultrasound image 50.

Note that the trajectory prediction 48 operates to compute the predicted trajectory 54 of the interventional instrument 10 even before the interventional instrument 10 penetrates the perineum Per, as shown in FIG. 1. In a preferred workflow, the surgeon presses the tip of the interventional instrument 10 against the perineum Per as shown in FIG. 1 in order to stabilize the position of the interventional instrument. The ultrasound imaging 42 receives the predicted trajectory 54 and superimposes it on the prostate ultrasound image 50 as a superimposed predicted trajectory representation 56. In this way, the surgeon is visually informed of the predicted trajectory 54 of the interventional instrument 10—if the trajectory is not acceptable then he or she can re-position the interventional instrument 10 and repeat the process until the predicted trajectory 54 as represented by its superimposed representation 56 on the prostate ultrasound image 50 is satisfactory to the surgeon.

With reference to FIG. 2, after the surgeon is satisfied with the predicted trajectory 54 he or she can proceed with the focal prostate intervention by pushing the interventional instrument 10 into the perineum Per in order to penetrate through the perineum Per and into the prostate Pr. The precise mechanics of this operation depends upon the configuration of the interventional instrument 10 and of the movable end 32 of the CMM 20. For example, in some types of interventional instrument, the instrument includes coaxial inner and outer tubular components and the inner tubular component is extended out of the inner tubular component to penetrate the perineum Per and thence into the prostate Pr. In this case the sleeve or other mount of the movable end 32 of the CMM 20 can be rigidly secured to the outer tubular component of the interventional instrument 10. In other types of interventional instrument, the entire straight end of the instrument is moved as a unit—in these embodiments, the movable end 32 of the CMM 20 can be constructed as a sleeve secured partway or all the way around the straight end of the interventional instrument, with the interventional instrument able to slide axially through the sleeve to perform the intervention in which the tip of the interventional instrument penetrates the perineum Per and into the prostate Pr. As shown in FIG. 2, as this occurs the end of the prostate intervention instrument 10 enters into the FOV of the prostate ultrasound image 50 and, in the illustrated embodiment, is visible as a tip image 58. Optionally, the trajectory prediction 58 may continue to operate based on the CMM position decoding 46 to produce the predicted trajectory 54 and its representation 56 in the image. Alternatively, the predicted trajectory may be terminated in response to the end of the prostate intervention instrument 10 coming into the FOV of the prostate ultrasound image 50 since at that point the surgeon can be guided by the visible tip image 58.

If the optional 3D tracking 44 is provided, then the portion of the interventional instrument 10 that has entered the FOV of the prostate ultrasound image 50 can be tracked solely by the 3D tracking 44 instead of relying on the predicted trajectory 56 determined using the CMM position decoding 46. As another option in this case, the tip and/or the shaft of the interventional instrument may be tracked as a weighted combination of the position and orientation of the interventional instrument as indicated by the 3D tracking 44 and the predicted trajectory 56 determined using the CMM position decoding 46. This approach provides advantageous redundancy in case one of these tracking modalities produces erroneous results. In some such redundant tracking embodiments, if the two tracking methods provide results that differ by more than a threshold amount then a visual and/or audio alarm is activated to warn the surgeon that either the tracking may be unreliable or needle bending may have occurred that is causing this discrepancy.

Figure 3:
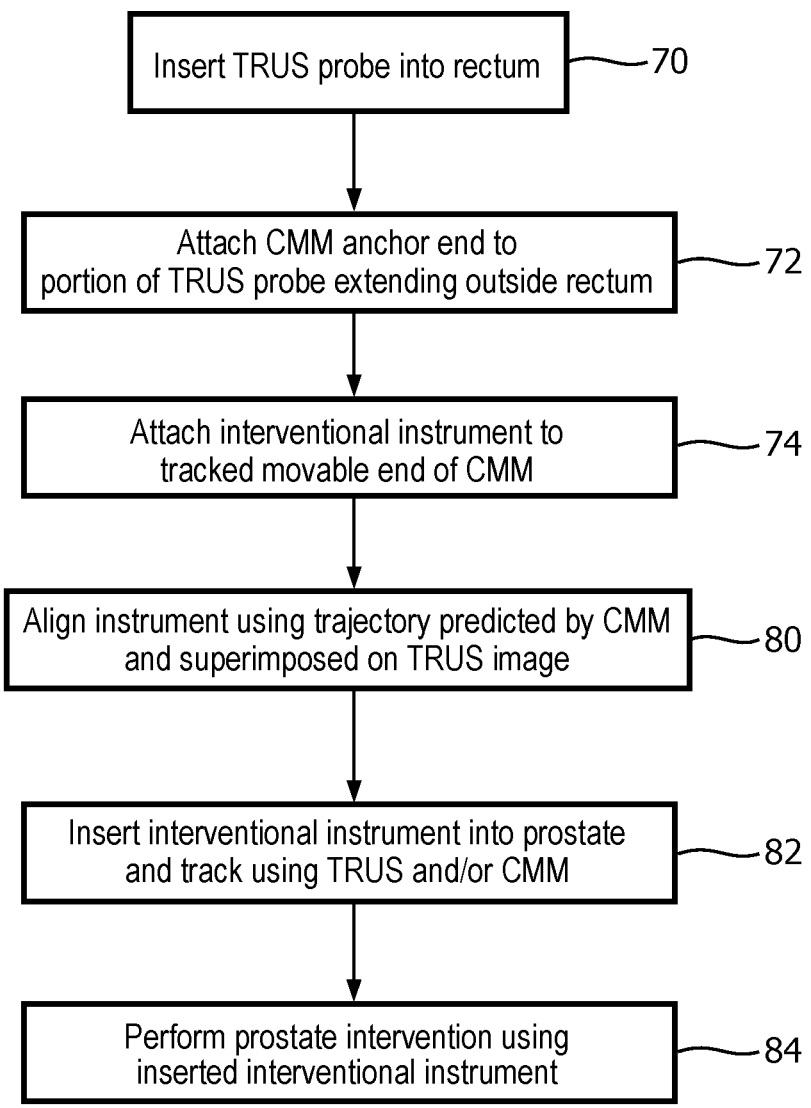
FIG. 3 shows a flow diagram of a focused prostate intervention suitably performed by the device of FIGS. 1 and 2.

With reference to FIG. 3, a focal prostate intervention performed using the illustrative device described with reference to FIGS. 1 and 2 begins with an operation 70 in which the TRUS probe 12 is inserted into the rectum Rec of the patient. In an operation 72, the anchor end 30 of the CMM 20 is attached to the portion of the TRUS probe 12 extending outside the rectum Rec. (Alternatively, the CMM could be attached before the TRUS probe is inserted into the rectum). In an operation 74, the interventional instrument 10 is attached to the movable end 32 of the CMM 20. At this point the guidance device is set up, and the (preferably video) ultrasound imaging is initiated. In an operation 80, the interventional instrument 10 is aligned with the target (e.g. suspected or known cancerous tumor or region of the prostate Pr). This alignment 80 is done using the predicted trajectory 54 and more particularly by visually observing the representation 56 of this trajectory superimposed on the prostate ultrasound image 50. Once the surgeon is satisfied with the instrument alignment, in an operation 82 the surgeon inserts the interventional instrument through the perineum Per and into the prostate Pr while tracking the insertion process using the ultrasound imaging provided by the TRUS probe 12 and/or the predicted trajectory 54 provided by the CMM 20, or a weighted combination of these two. In an operation 84, the prostate intervention is performed using the inserted interventional instrument 10. This may, for example, entail acquiring a biopsy sample, or depositing radioactive brachytherapy seeds, or performing RF ablation or cryoablation, or so forth. Optionally, the foregoing process may be repeated to perform the intervention on multiple target areas of the prostate. In such a case, the operations 70, 72 generally do not need to be repeated, and the operation 74 may or may not be repeated depending upon reusability of the interventional instrument 10.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A transperineal prostate intervention guidance device comprising:
   a transrectal ultrasound (TRUS) probe including an ultrasound transducer or transducer array;
   a coordinate measurement machine (CMM) configured for attachment to the TRUS probe and configured to track the position and orientation of a prostate intervention instrument in a frame of reference of the TRUS probe, the CMM comprising a single articulated arm including arm segments connected by encoding joints and having an anchor end configured for attachment to the TRUS probe and a movable end configured for attachment with the prostate intervention instrument; and
   an electronic processor programmed to:
      compute a predicted trajectory of the prostate intervention instrument in the frame of reference of the TRUS probe using the CMM from a position and orientation of the movable end of the articulated arm determined from encoding values of the encoding joints, and
      generate a prostate ultrasound image from ultrasound data collected by the TRUS probe with a representation of the predicted trajectory of the prostate intervention instrument superimposed on the prostate ultrasound image.

2. The transperineal prostate intervention guidance device of claim 1 wherein the electronic processor is further programmed to:
   determine position and orientation of a portion of the prostrate intervention instrument in a field of view (FOV) of the prostate ultrasound image using ultrasound signals generated in response to ultrasound transmissions output by the TRUS probe.

3. The transperineal prostate intervention guidance device of claim 2 wherein the electronic processor is programmed to determine the position and orientation of the portion of the prostrate intervention instrument in the FOV of the prostate ultrasound image using the ultrasound signals comprising one of (i) the prostate ultrasound image and (ii) signals generated by ultrasound sensors disposed on the prostate intervention instrument in response to ultrasound transmissions output by the TRUS probe.

4. The transperineal prostate intervention guidance device of claim 3 wherein the electronic processor is programmed to determine the position and orientation of the portion of the prostrate intervention instrument in the FOV of the prostate ultrasound image further using the predicted trajectory of the prostate intervention instrument.

5. The transperineal prostate intervention guidance device of claim 4 wherein the electronic processor is programmed to determine the position and orientation of the portion of the prostate intervention instrument in the FOV of the prostate ultrasound image as a weighted combination of:
   (1) an ultrasound-based position and orientation of the portion of the prostrate intervention instrument in the FOV of the prostate ultrasound image determined using the ultrasound signals generated in response to the ultrasound transmissions output by the TRUS probe; and
   (2) the predicted trajectory of the prostate intervention instrument.

6. A transperineal prostate intervention device comprising:
   a prostate intervention instrument;
   a transrectal ultrasound (TRUS) probe including an ultrasound transducer or transducer array; and
   a mechanical coordinate measurement machine (CMM) attached to the TRUS probe and configured to track the prostate intervention instrument, the mechanical CMM including a single articulated arm with a plurality of encoding joints, and an anchor end attached to the TRUS probe and a movable end attached to the prostate intervention instrument.

7. The transperineal prostate intervention device of claim 6 wherein the plurality of encoding joints of the mechanical CMM includes at least three encoding joints.

8. The transperineal prostate intervention device of claim 6 wherein the prostate intervention instrument is a biopsy needle, a brachytherapy seed delivery instrument, a tissue ablation instrument, or a hollow cannula.

9. The transperineal prostate intervention device of claim 6 further comprising:
   an electronic processor programmed to compute a predicted trajectory of the prostate intervention instrument in a frame of reference of the TRUS probe using the mechanical CMM attached to the TRUS probe.

10. The transperineal prostate intervention device of claim 9 further comprising:
    a display component;
    wherein the electronic processor is further programmed to cause the display component to display a prostate ultrasound image generated from ultrasound data collected by the TRUS probe with a representation of the predicted trajectory of the prostate intervention instrument superimposed on the displayed prostate ultrasound image.

11. The transperineal prostate intervention device of claim 9 wherein the electronic processor is further programmed to determine position and orientation of a portion of the prostate intervention instrument in a field of view (FOV) of the prostate ultrasound image using ultrasound signals generated in response to ultrasound transmissions output by the TRUS probe.

12. The transperineal prostate intervention device of claim 11 wherein the electronic processor is programmed to determine the position and orientation of the portion of the prostrate intervention instrument in the FOV of the prostate ultrasound image using the ultrasound signals comprising one of (i) the prostate ultrasound image and (ii) signals generated by ultrasound sensors disposed on the prostate intervention instrument in response to ultrasound transmissions output by the TRUS probe.

13. The transperineal prostate intervention device of claim 11 wherein the electronic processor is programmed to determine the position and orientation of the portion of the prostate intervention instrument in the FOV of the prostate ultrasound image using both the ultrasound signals generated in response to the ultrasound transmissions output by the TRUS probe and the predicted trajectory of the prostate intervention instrument.

14. A transperineal prostate intervention guidance method comprising:
    displaying an ultrasound image of a prostate generated from ultrasound data acquired by a transrectal ultrasound (TRUS) probe;
    during the displaying, computing a predicted trajectory of a prostate intervention instrument in a frame of reference of the TRUS probe using a mechanical coordinate measurement machine (CMM) anchored to the TRUS probe, the mechanical CMM comprising a single articulated arm with a plurality of encoding joints, an anchor end that is anchored to the TRUS probe, and a movable end that is attached to the prostate intervention instrument; and
    superimposing a representation of the predicted trajectory of the prostate intervention instrument on the displayed ultrasound image of the prostate.

15. The transperineal prostate intervention guidance method of claim 14, wherein the computing and superimposing operations are performed with no portion of the prostate intervention instrument in the field of view of the ultrasound image of the prostate.

* * * * *